United States Patent [19]

Catt

[11] Patent Number: Plant 7,537

[45] Date of Patent: May 28, 1991

[54] *SPIREA JAPONICA* — LISP VARIETY

[75] Inventor: Peter Catt, Greatham, Great Britain

[73] Assignee: The Conard-Pyle Company, West Grove, Pa.

[21] Appl. No.: 478,528

[22] Filed: Feb. 12, 1990

[51] Int. Cl.[5] ..... A01H 5/00

[52] U.S. Cl. ..... Plt./54

[58] Field of Search ..... Plt./54

[56] References Cited

U.S. PATENT DOCUMENTS

P.P. 5,834 12/1986 Huber ..... Plt. 54

*Primary Examiner*—James R. Feyrer

*Attorney, Agent, or Firm*—Burns, Doane, Swecker & Mathis

[57] ABSTRACT

The invention relates to a new and distinct variety of *Spirea japonica* which originated as a natural cross while growing in a cultivated area. The new variety is of the deciduous type and exhibits a bushy compact growth habit, foliage which is of an attractive golden/yellow coloration during the spring, the abundant formation of attractive bright pink flowers over an extended period of time, and good hardiness. The new variety is particularly suited for growing as a brilliant new decorative shrub for the summer garden and does well in full sun.

1 Drawing Sheet

SUMMARY OF THE INVENTION

The present invention relates to a new and distinct variety of *Spirea japonica* which originated as a natural cross and was discovered while growing among a number of seedlings in a cultivated area in England. It is believed that the parents of the new variety were *Spirea japonica* 'Little Princess' and *Spirea japonica* 'Gold Flame'. Neither of these parent plants are patented in the United States. I was attracted to the plant of the new variety because of its distinctive appearance as discussed hereafter. Had the plant of new variety not been preserved, it would have been lost to mankind.

The new variety can be distinguished from its parent varieties and from all other known varieties of *Spirea japonica*, and can be identified by the following combination characteristics:

(a) a more compact growth habit than *Spirea japonica* 'Gold Flame'.
(b) the formation of foliage which during the spring exhibits a golden/yellow coloration which persists longer and is more stable than that of *Spirea japonica* 'Gold Flame'.
(c) the exhibition of a profuse flowering habit from approximately May until October when grown at West Grove, Pa., and
(d) the capability of undergoing asexual propagation on stable and homogeneous basis.

It has been found that the majority of 18-month old container grown plants of the new variety measure approximately 8 to 9 inches in height and 20 to 22 inches in breadth when grown at West Grove, Pa.

The new variety has exhibited good hardiness and has survived without injury when over-wintered in containers above ground at West Grove, Pa.

Asexual propagation of the new variety has been accomplished by the use of cuttings in England and at West Grove, Pa. It has been demonstrated that the unique combination of characteristics has been established and is well transmitted to successive generations.

The new variety has been named the LISP variety, and is being marketed by the The Conard-Pyle Company of West Grove, Pa. under the Golden Princess trademark.

BRIEF DESCRIPTION OF THE PHOTOGRAPH

The accompanying photograph of FIG. 1 illustrates a typical plant of new variety in color as nearly true as it is reasonably possible to make the same in a color illustration of this character. The distinctive coloration of the foliage and the blossom coloration are apparent. The photograph was taken of a plant of the new variety while being grown at West Grove, Pa.

DETAILED DESCRIPTION

Figure 1:
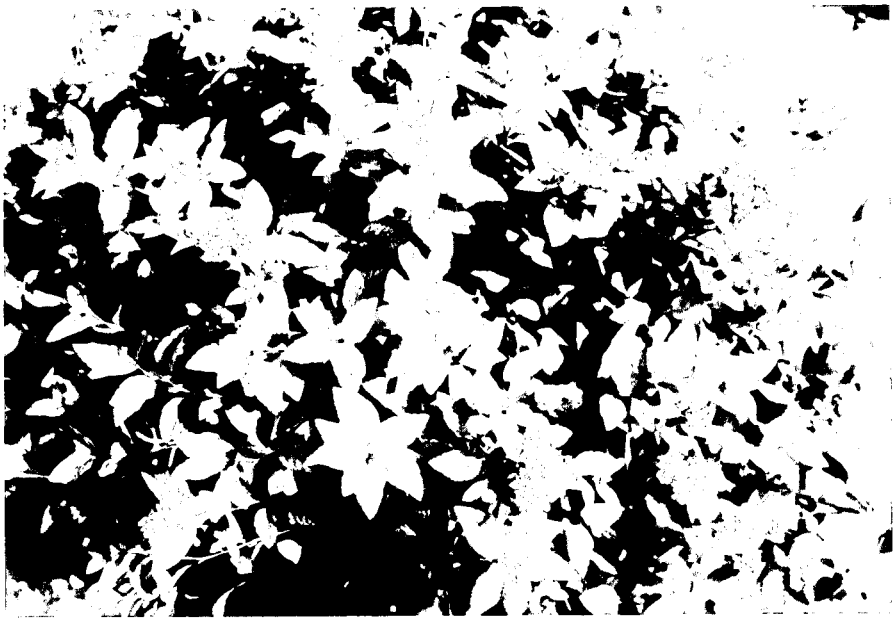

The following is a detailed description of the new variety while present as 18-month old plants growing in 2-gallon containers at West Grove, Pa. The color terminology is in accordance with the RHS Colour Chart of The Royal Horticultural Society, London, England, except where general color terms of ordinary dictionary significance are used.

Type: Hardy outdoor flowering shrub for garden decoration and landscape use.

Parentage: Believed to be *Spirea japonica* 'Little Princess' × *Spirea japonica* 'Gold Flame'.

Class: *Spirea japonica.*

Foliage:

*Type.*—Deciduous. The leaves are typical of the species, ovate with an obtuse base and an acute apex, serration is single and fairly regular, young leaves are curling toward the lower surface near the tip, and the leaves are concave along the central vein and tend to flatten upon maturity.

*Stem habit.*—Helix close to but superior to 120 degrees.

*General Aspect.*—Dense, bright and yellowish.

*Size.*—The mature leaves on the main stem are approximately 4 to 4.5 cm. in length on average, and approximately 2.5 cm. in maximum breadth on average.

*Petiole.*—Small, approximately 3 mm. on average on both young and mature leaves, the coloration is yellowish green on the upper surface and reddish on the lower surface on young leaves turning yellowish green on mature leaves.

*Color.*—Mature leaves of spring foliage observed during May on the upper surface are sap green, Yellow-Green Group 150B, turning to Yellow-Green Group 144B near the base of the leaf, and on the under surface are sap green, Yellow-Green Group 150C. Young leaves of summer foliage observed during August on the upper surface are Yellow-Green Group 151A, and on the under surface are Yellow-Green Group 146D. Mature leaves on summer foliage observed during August on the upper surface are Yellow-Green Group 144B and on the under surface are Yellow-Green Group 139D. Young leaves on fall foliage observed during early October on the upper surface are Yellow-Green Group 151A strongly tinted with Greyed-Red Group 178B from the apex down, and on the under surface are Greyed-Red Group 182B sometimes tinted with Yellow-Green Group 146D. Mature leaves on fall foliage observed during early October on the upper surface are Yellow-Green Group 144B strongly tinted with Greyed-Red Group 178B from the apex down, and on the under surface are Yellow-Green Group 146D strongly and unevenly suffused with Greyed-Red Group 182B but much less than on the younger leaves. Young stems are yellowish green turning to Greyed-Orange Group 164A. Mature stems are Greyed-Orange Group 165A.

Flowers:

*Disposition.*—Bisexual flowers typical of the species are borne in compound corymbs on normal stems of the current year's growth. They commonly are borne freely and continuously outdoors from May until October at West Grove, Pa. There is usually one and sometimes two of these corymbs per stem. Commonly approximately 22 to 25 florets on average appear per corymb. The peduncle is short (e.g., approximately 1 cm. in length) and is reddish in coloration. The buds also are typical of the species.

*Color.*—Red-Purple Group 66C.

*Petals.*—Commonly five in number.

*Pistils.*—Commonly five in number, the styles are reddish in coloration, and the stigmas are yellowish in coloration.

*Stamens.*—Commonly approximately 30 on average, very irregular in length, the anthers are greyish in coloration, and the filaments are reddish in coloration.

*Size.*—When open, the diameter of the bloom is approximately 7 to 8 mm. on average, and the width of the corymbs is approximately 3 to 5 cm.

*Fruit.*—Commonly approximately five seeds are formed per floret, having the general configuration of a cone with the apex curling outwards from the center of the floret. The base of the fruit is greenish in coloration and tends to change to brown near the top.

I claim:

1. A new and distinct variety of *Spirea japonica* substantially as illustrated and described and characterized by:

(a) a more compact growth habit than *Spirea japonica* 'Gold Flame'.

(b) the formation of foliage which during the spring exhibits a golden/yellow coloration which persists longer and is more stable than that of *Spirea japonica* 'Gold Flame'.

(c) the exhibition of a profuse flowering habit from approximately May until October when grown at West Grove, Pa., and (d) the capability of undergoing asexual propagation on a stable and homogenous basis.

* * * * *